United States Patent [19]
Parkes et al.

[11] Patent Number: 5,580,999
[45] Date of Patent: Dec. 3, 1996

[54] ALCOHOLS

[75] Inventors: Kevin E. B. Parkes, Letchworth; Sally Redshaw, Stevenage; Gareth J. Thomas, Welwyn, all of Great Britain

[73] Assignee: Hoffmann-La Roche Inc., Nutley, N.J.

[21] Appl. No.: 439,611

[22] Filed: May 12, 1995

Related U.S. Application Data

[62] Division of Ser. No. 128,978, Sep. 29, 1993, Pat. No. 5,451,678, which is a continuation of Ser. No. 615,204, Nov. 19, 1990, abandoned.

[30] Foreign Application Priority Data

Dec. 11, 1989 [GB] United Kingdom ............... 8927915

[51] Int. Cl.$^6$ .................................................. C07C 247/04
[52] U.S. Cl. ..................... 552/10; 552/1; 544/373; 544/386; 544/402; 546/85; 546/87; 546/145; 546/146; 546/147; 548/200; 548/201; 548/453; 548/455; 548/530; 548/551
[58] Field of Search ............................................. 552/10

[56] References Cited

U.S. PATENT DOCUMENTS

| | | | |
|---|---|---|---|
| 3,901,897 | 8/1975 | Hauck et al. | 546/143 |
| 4,123,543 | 10/1978 | Jonsson et al. | 548/465 |
| 4,325,877 | 4/1982 | Metcalf et al. | 260/349 |
| 4,329,473 | 5/1982 | Almquist et al. | 548/465 |
| 4,898,977 | 2/1990 | Herold et al. | 564/191 |
| 5,157,041 | 10/1992 | Handa et al. | 574/314 |
| 5,354,866 | 10/1994 | Kempf et al. | 546/265 |

FOREIGN PATENT DOCUMENTS

| | | | |
|---|---|---|---|
| 163437 | 6/1958 | France | 548/465 |
| 57-165357 | 10/1982 | Japan | 552/1 |
| 63-174960 | 7/1988 | Japan | 552/10 |
| 933968 | 4/1961 | United Kingdom | 548/465 |
| 8403044 | 2/1984 | WIPO . | |

OTHER PUBLICATIONS

McQuade et al, Science, 247:454–456, 1990.
Meek et al, Nature 343:90–92, 1990.
Yasuda et al., Chem. Lett., (1), 31–34, 1985.
Bau et al. Rev. Latinoam. Quim 5(4):211–214, 1974.
Stefanec et al., Chemical Abstract, vol. 54, No. 21, 22572f, 1960.
CA 102(19):166520u, 1990.
Bessodes et al, Tetrahedron letters, 25:5899–5902, 1984.
Mulzer et al., Liebegs Ann. Chem., pp. 445–448, 1988.
Luhy et al, J. Org. Chem., 52:1487–1492, 1987.
Dreyer et al., PNAS, USA, 86:9752–9756, 1989.
Roberts et al., Science, 248:358–361, 1990.
Takano et al, Heterocycles, 29(2):249–252, 1989.
Onaka et al, J. Org. Chem. 54(5):1116–1123, 1989.
Paquette, J. Org. Chem., 53(2)):5185–5187, 1988.
Onaka et al., Chem. Lett. 8:1327–1328, 1986.
Behrens, J. Org. Chem., 50(26):5696–5704, 1985.
Maruoka et al., Chem. Lett., 5:599–602, 1985.
Mulzer et al., J. Org. Chem., 51(26):5294–5299, 1986.
Paul et al, J. Pharm. Sci, 67(5):642–645, 1978.

*Primary Examiner*—Shailendra Kumar
*Attorney, Agent, or Firm*—George W. Johnston; William H. Epstein; Catherine R. Smith

[57] ABSTRACT

Novel alcohols of the formula

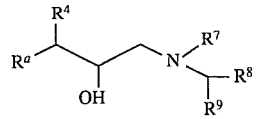

I wherein $R^a$ is azido or phthalimido, $R^4$ is alkyl, cycloalkyl, cycloalkylalkyl, aryl or aralkyl, $R^7$ and $R^8$ together are a trimethylene or tetramethylene group which is optionally substituted by hydroxy, alkoxycarbonylamino or acylamino or in which one —$CH_2$— group is replaced by —NH—, -N(alkoxycarbonyl)-,-N(acyl)- or —S—or which carries a fused cycloalkane, aromatic or heteroaromatic ring, and $R^9$ is alkoxycarbonyl, monoalkylcarbamoyl, monoaralkylcarbamoyl, monoarylcarbamoyl or a group of the formula

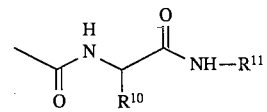

in which $R^{10}$ and $R^{11}$ each is alkyl, are described along with a process for their manufacture. These alcohols are useful as intermediates, for example in the manufacture of amino acid derivatives having antiviral activity.

2 Claims, No Drawings

ALCOHOLS

This is a division of application Ser. No. 08/128,978, now U.S. Pat. No. 5,451,678 filed Sep. 29, 1993, which is a continuation of application Ser. No. 07/615,204, filed Nov. 19, 1990, now abandoned.

SUMMARY OF THE INVENTION

The present invention relates to novel alcohols. More particularly, the invention is concerned with novel alcohols, a process for the manufacture thereof and novel intermediates in said process.

The novel alcohols provided by the present invention have the general formula

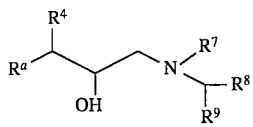

wherein $R^a$ represents azido or phthalimido, $R^4$ represents alkyl, cycloalkyl, cycloalkylalkyl, aryl or aralkyl, $R^7$ and $R^8$ together represent a trimethylene or tetramethylene group which is optionally substituted by hydroxy, alkoxycarbonylamino or acylamino or in which one —$CH_2$— group is replaced by —NH—, -N(alkoxycarbonyl)-, -N(acyl)- or —S— or which carries a fused cycloalkane, aromatic or heteroaromatic ring, and $R^9$ represents alkoxycarbonyl, monoalkylcarbamoyl, monoaralkylcarbamoyl, monoarylcarbamoyl or a group of the formula

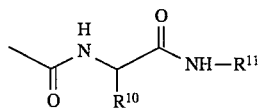

in which $R^{10}$ and $R^{11}$ each represent alkyl.

The alcohols of formula I are valuable intermediates in chemical syntheses. For example, they can be converted in the manner described in more detail hereinafter into amino acid derivatives of the formula

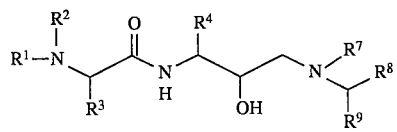

wherein $R^1$ represents alkoxycarbonyl, aralkoxycarbonyl, alkanoyl, cycloalkylcarbonyl, aralkanoyl, aroyl, heterocyclylcarbonyl, alkylsulphonyl, arylsulphonyl, monoaralkylcarbamoyl, cinnamoyl or α-aralkoxycarbonylaminoalkanoyl and $R^2$ represents hydrogen, or $R^1$ and $R^2$ together with the nitrogen atom to which they are attached represent a cyclic imide group of the formula

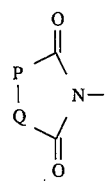

(a)

in which P and Q together represent an aromatic system, $R^3$ represents alkyl, cycloalkyl, aryl, aralkyl, heterocyclylalkyl, cyanoalkyl, alkylthioalkyl, alkylsulphinylalkyl, carbamoylalkyl or alkoxycarbonylalkyl and $R^4$, $R^7$, $R^8$ and $R^9$ have the significance given earlier.

These amino acid derivatives possess valuable pharmacological properties. In particular, they inhibit proteases of viral origin and can be used in the prophylaxis or treatment of viral infections, particularly of infections caused by HIV and other retroid viruses (see British Patent Application No. 8908035 and corresponding U.S. Ser. No. 07/362,621 U.S. Pat. No. 5,157,041).

DETAILED DESCRIPTION OF THE INVENTION

As used in this Specification, the term "alkyl", alone or in combination, means a straight-chain or branched-chain alkyl group containing a maximum of 8, preferably a maximum of 4, carbon atoms such as methyl, ethyl, n-propyl, isopropyl, n-butyl, isobutyl, sec.butyl, tert.butyl, pentyl, hexyl and the like.

The term "alkoxy", alone or in combination, means an alkyl ether group, the term "alkyl" being defined as above, examples of such alkyl ether group being methoxy, ethoxy, n-propoxy, isopropoxy, n-butoxy, isobutoxy, sec.butoxy, tert.butoxy and the like.

The term "cycloalkylalkyl" means an alkyl group (where alkyl is defined as above) which is substituted by a cycloalkyl group containing 3–8, preferably 3–6, carbon atoms such as cyclopropyl, cyclobutyl, cyclopentyl, cyclohexyl and the like.

The term "aryl", alone or in combination, means a phenyl or naphthyl group which optionally carries one or more substituents selected from alkyl, alkoxy, halogen, hydroxy, amino and the like, such as phenyl, p-tolyl, 4-methoxyphenyl, 4-tert.butoxyphenyl, 4-fluorophenyl, 4-chlorophenyl, 4-hydroxyphenyl, 1-naphthyl, 2-naphthyl etc.

The term "aralkyl", alone or in combination, means an alkyl group as defined earlier in which one hydrogen atom is replaced by an aryl group as defined earlier, such as benzyl, 2-phenylethyl and the like.

The term "aralkoxycarbonyl", alone or in combination, means a group of the formula —C(O)—O-aralkyl, in which the term "aralkyl" has the definition given above, such as benzyloxycarbonyl, etc.

The term "alkanoyl", alone or in combination, means an acyl group derived from an alkanecarboxylic acid such as acetyl, propionyl, butyryl, valeryl, 4-methylvaleryl etc.

The term "cycloalkylcarbonyl" means an acyl group derived from a monocyclic or bridged cycloalkanecarboxylic acid such as cyclopropanecarbonyl, cyclohexanecarbonyl., adamantanecarbonyl, etc., or from a benz-fused monocyclic cycloalkanecarboxylic acid which is optionally substituted. by, for example, alkanoylamino, such as 1,2,3,4-tetra-hydro-2-naphthoyl, 2-acetamido-1,2,3,4-tetrahydro-2-naphthoyl.

The term "aralkanoyl" means an acyl group derived from an aryl-substituted alkanecarboylic acid such as phenylacetyl, 3-phenylpropionyl (hydrocinnamoyl), 4-phenylbutyryl, (2-naphthyl)acetyl, 4-chlorohydrocinnamoyl, 4-aminohydrocinnamoyl, 4-methoxyhydrocinnamoyl, etc.

The term "aroyl" means an acyl group derived from an aromatic carboxylic acid: for example an optionally substituted benzoic or naphthoic acid such as benzoyl, 4-chlorobenzoyl, 4-carboxybenzoyl, 4-(benzyloxycarbonyl)-benzoyl, 1-naphthoyl, 2-naphthoyl, 6-carboxy-2-naphthoyl, 6-(benzyloxycarbonyl)-2-naphthoyl, 3-benzyloxy-2-naphthoyl, 3-hydroxy-2-naphthoyl, 3-(benzyloxyformamido)-2-naphthoyl, etc.

The heterocyclyl portion of a heterocyclylcarbonyl or heterocyclylalkyl group is a saturated, partially unsaturated or aromatic monocyclic, bicyclic or tricyclic heterocycle which contains one or more hereto atoms selected from nitrogen, oxygen and sulphur, which is optionally substituted on one or more carbon atoms by halogen, alkyl, alkoxy, oxo etc and/or on a secondary nitrogen atom (i.e. —NH—) by alkyl, aralkoxycarbonyl, alkanoyl, phenyl or phenylalkyl or on a tertiary nitrogen atom (i.e. =N—) by oxido and which is attached via a carbon atom. Examples of such heterocyclyl groups are pyrrolidinyl, piperidinyl, piperazinyl, morpholinyl, thiamorpholinyl, pyrrolyl, imidazolyl (e.g. imidazol-4-ol, 1-benzyloxycarbonylimidazol-4-yl, etc), pyrazolyl, pyridyl, pyrazinyl, pyrimidinyl, furyl, thienyl, triazolyl, oxazolyl, thiazolyl, indolyl (e.g. 2-indolyl etc), quinolyl (e.g. 2-quinolyl, 3-quinolyl, 1-oxido-2-quinolyl etc), isoquinolyl (e.g. 1-isoquinolyl, 3-isoquinolyl etc), tetrahydroquinolyl (e.g. 1,2,3,4-tetrahydro-2-quinolyl etc), 1,2,3,4-tetrahydroisoquinolyl (e.g. 1,2,3,4-tetrahydro-1-oxoisoquinolyl etc), quinoxalinyl, β-carbolinyl and the like.

The term "halogen" means fluorine, chlorine, bromine or iodine.

A cinnamoyl group denoted by $R^1$ can be unsubstituted or can carry on the phenyl ring one or more substituents selected from alkyl, alkoxy, halogen, nitro and the like.

The aromatic system denoted by P and Q together in formula (a) given earlier can be monocyclic (e.g. 1,2-phenylene or thienylene) or polycyclic (e.g. 1,2-naphthylene, 2,3-naphthylene, 1,8-naphthylene, 2,3-anthrylene, etc.) and can be unsubstituted or substituted by one or more substituents selected from alkyl, alkoxy, halogen and the like.

As mentioned earlier, a trimethylene or tetramethylene group denoted by $R^7$ and $R^8$ together can be optionally substituted by a hydroxy group or an alkoxycarbonylamino group (e.g. tert.butoxycarbonylamino) or an acylamino group (i.e. an alkanoylamino, cycloalkylcarbonylamino, aralkanoylamino or aroylamino group). Alternatively, one —CH$_2$— group of a trimethylene or tetramethylene group denoted by $R^7$ and $R^8$ together can be replaced by —NH—, -N(alkoxycarbonyl)-, for example -N(tert.butoxycarbonyl)-, -N(acyl)- or —S—. When a trimethylene or tetramethylene group denoted by $R^7$ and $R^8$ together carries a fused cycloalkane ring, this can be, for example, a fused cycloalkane ring containing 3–6 carbon atoms such as a fused cyclopentane, cyclohexane or like ring and when the trimethylene or tetramethylene group carries a fused aromatic or heteroaromatic ring, this can be, for example, a fused benzene, indole or thiophene ring which can be optionally substituted on one or more carbon atoms by halogen, alkyl, alkoxy etc. Thus, —N($R^7$)—CH($R^8$)($R^9$) can represent, for example, one of the following groups:

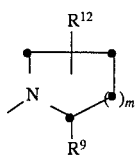

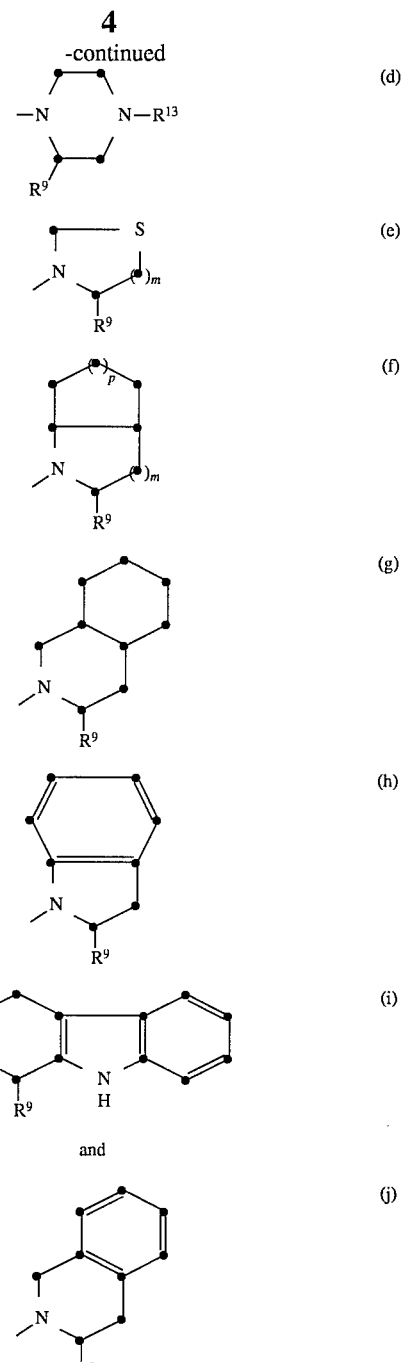

wherein $R^9$ has the meaning given above, $R^{12}$ represents hydrogen, hydroxy, alkoxycarbonylamino or acylamino, $R^{13}$ represents hydrogen, alkoxycarbonyl or acyl, m stands for 1 or 2 and p stands for 1 or 2.

The alcohols of formula I contain at least two asymmetric carbon atoms and can therefore exist in the form of optically pure diastereoisomers, mixtures of diastereoisomers, diastereoisomeric racemates or mixtures of diastereoisomeric racemates. The present invention includes within its scope all of these forms.

In formula I above, $R^a$ preferably represents phthalimido. $R^4$ preferably represents aralkyl, especially benzyl. Preferably, —N($R^7$)—CH($R^8$)($R^9$) represents a group of formula (g) above in which $R^9$ represents monoalkylcarbamoyl, preferably tert.butylcarbamoyl.

From the foregoing it will be appreciated that especially preferred alcohols of formula I are those in which $R^a$ represents phthalimido, $R^4$ represents benzyl and —N($R^7$)—CH($R^8$)($R^9$) represents a group of formula (g) in which $R^9$ represents tert.butylcarbamoyl.

N-tert.Butyl-decahydro-2-[2(R)-hydroxy-4-phenyl-3(S)-phthalimidobutyl]-(4aS,8aS)-isoquinoline-3(S)-carboxamide is a particularly preferred alcohol of formula I above.

2-[3(S)-Azido-2(R)-hydroxy-4-phenylbutyl]-N-tert.butyl-decahydro-(4aS,8aS)-isoquinoline-3(S)-carboxamide is a further example of a preferred compound of formula I above.

The alcohols of formula I above can be manufactured in accordance with this invention by the following procedure:

(a) reacting an epoxide of the general formula

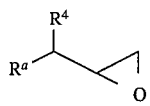   III wherein $R^a$ and $R^4$ have the meaning given above, with a compound of the general formula

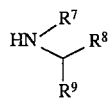   IV wherein $R^7$, $R^8$ and $R^9$ have the meaning given above, or (b) for the manufacture of an alcohol of formula I in which $R^a$ represents azido, reacting a compound of the general formula

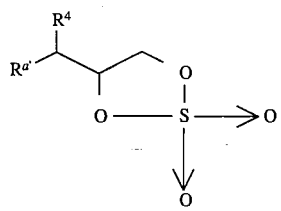   V wherein $R^{a'}$ represents azido and $R^4$ has the meaning given above, with a compound of formula IV above.

The reaction of an epoxide of formula III with a compound of formula IV in accordance with embodiment (a) of the process is conveniently carried out in an inert organic solvent, such as an alkanol (e.g. methanol etc), dimethylformamide or the like and at an elevated temperature, preferably from about 60° C. to about 120° C.

The reaction of a compound of formula V with a compound of formula IV in accordance with embodiment (b) of the process is conveniently carried out in an inert organic solvent such as an ether (e.g. tetrahydrofuran etc) and at about room temperature.

The epoxides of formula III, which are used as starting materials in embodiment (a) of the process, are novel and also form an object of the present invention.

The epoxides of formula III in which $R^a$ represents azido can be prepared, for example, by converting a compound of the general formula

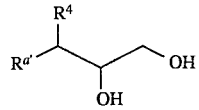   VI wherein $R^{a'}$ and $R^4$ have the meaning given earlier, in a manner known per se into a compound of the general formula

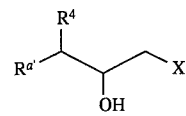   VII wherein $R^{a'}$ and $R^4$ have the meaning given earlier and X represents a leaving atom or group such as a halogen atom (e.g. a chlorine or bromine atom), an alkanesulphonyloxy group (e.g. methanesulphonyloxy etc) or an aromatic sulphonyloxy group (e.g. benzenesulphonyloxy, p-toluenesulphonyloxy, 2,4,6-tri-isopropylbenzenesulphonyloxy etc), and cyclizing the resulting compound of formula VII, likewise in a manner known in the art, for example by treatment with an alkali metal hydroxide in an alkanol such as potassium hydroxide in ethanol, to give a desired epoxide of formula III.

The compounds of formula VII are novel and also form an object of the present invention. The compounds of formula VI are known compounds or analogues of known compounds which can be prepared by those skilled in the art in a manner similar to the preparation of the known compounds. In addition, the Examples which follow contain a detailed description of an alternative method for the preparation of a certain compound of formula VI.

The epoxides of formula III in which $R^a$ represents phthalimido can be prepared, for example, as illustrated in Reaction Scheme I below in which $R^{a''}$ represents phthalimido, $R^4$ has the meaning given above, Y represents alkylsulphonyl and Z' represents a hydroxy protecting group removable by hydrolysis (e.g. tetrahydropyranyl):

Reaction Scheme I

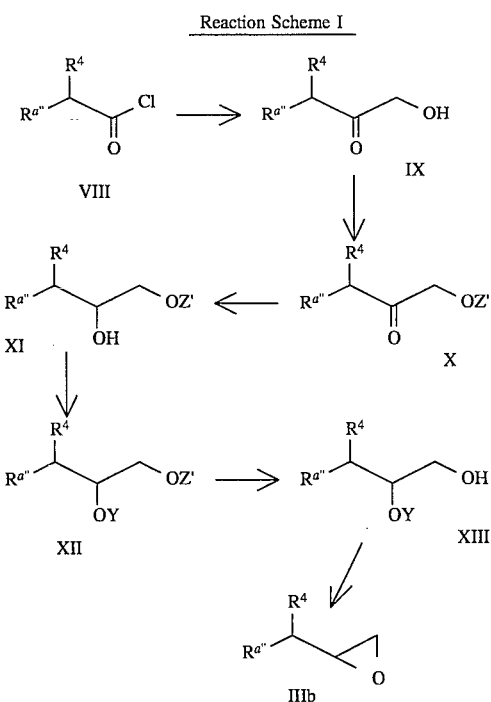

In the first step of Reaction Scheme I, a compound of formula VIII is reacted with a tris(trialkylsilyloxy)ethylene such as tris(trimethylsilyloxy)ethylene, preferably at an elevated temperature such as from about 90° C. to about 100° C., to give a compound of formula IX. This compound is then protected at the hydroxy group in a manner known to those skilled in the art, for example by reaction with dihydropyran, and the resulting compound of formula X is reduced at the carbonyl group also in a manner known in the art, such as by means of a complex metal hydride (e.g. sodium borohydride etc). The resulting compound of formula XI is then converted into a compound of formula XII by treatment with an alkanesulphonyl halide (e.g. methanesulphonyl chloride) according to conventional procedures and the compound of formula XII obtained is hydrolyzed in a manner known in the art (e.g. using p-toluenesulphonic acid) to give a compound of formula XIII. A compound of formula XIII is finally converted into an epoxide of formula IIIb by treatment with a base such as an alkali metal hydride (e.g. sodium hydride) or an alkali metal lower alkoxide (e.g. potassium tert.butoxide) in an inert organic solvent such as dimethylformamide etc.

In Reaction Scheme I, compounds IX through XIII may conveniently be represented by the general formula

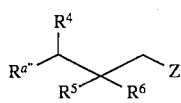
A wherein $R^{a''}$ is phthalimido, $R^4$ is alkyl, cycloalkyl, cycloalkylalkyl, aryl or aralkyl, $R^5$ is hydrogen, $R^6$ is hydroxy or alkylsulphonyloxy or $R^5$ and $R^6$ together are an oxo group, and Z is hydroxy or a hydroxy protecting group removable by hydrolysis, provided that when $R^6$ is hydroxy, Z is a hydroxy protecting group removable by hydrolysis.

The compounds of formula VIII above are known compounds or analogues of known compounds which can be prepared in a similar manner to the preparation of the known compounds, whereas the compounds of formulae IX to XIII are novel and also form objects of the present invention.

The compounds of formula IV, which are used as starting materials in embodiments (a) and (b) of the process described above, are known compounds or can be prepared readily from known compounds in a manner known to those skilled in the art, for example, by converting the carboxyl group in a corresponding carboxylic acid into the group $R^9$.

The compounds of formula V, which are used as starting materials in embodiment (b) of the process, are novel and also form an object of the present invention. They can be prepared, for example, by reacting a compound of formula VI above with thionyl chloride, preferably in an inert organic solvent such as a halogenated hydrocarbon (e.g. carbon tetrachloride etc) and at an elevated temperature, preferably at the reflux temperature of the reaction mixture, and oxidizing the reaction product in a known manner. Conveniently, the oxidation is carried out using ruthenium(III) chloride in the presence of an alkali metal periodate (e.g. sodium metaperiodate) at about room temperature. The reaction product is expediently oxidized in situ.

As mentioned earlier, the alcohols of formula I can be converted into amino acid derivatives of formula II which have valuable pharmacological properties. This conversion can be carried out, for example, by transforming the phthalimido or azido group $R^a$ in the alcohol into an amino group and reacting the resulting compound of the general formula

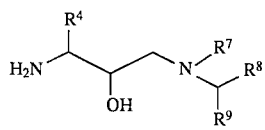
XIV wherein $R^4$, $R^7$, $R^8$ and $R^9$ have the meaning given above, with an acid of the general formula

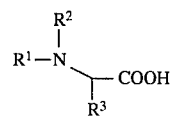
XV $R^1$, $R^2$ and $R^3$ have the meaning given above, or a reactive derivative thereof.

The transformation of the phthalimido or azido group $R^a$ in an alcohol of formula I into an amino group can be carried out according to methods known to those skilled in the art. For example, the phthalimido group can be transformed into the amino group by treatment with hydrazine or a primary amine (e.g. an alkylamine such as methylamine) and the azido group can be transformed into the amino group by catalytic hydrogenation.

The reaction of a compound of formula XIV with an acid of formula XV or a reactive derivative thereof can be carried out in accordance with methods well-known to those skilled in peptide chemistry. When an acid of formula XV is used, the reaction is preferably carried out in the presence of a condensation agent such as hydroxybenzotriazole and dicyclohexylcarbodiimide. This reaction is conveniently carried out in an inert organic solvent such as an ether (e.g. diethyl ether, tetrahydrofuran, etc.) or dimethylformamide at a low temperature, suitably from about $-10°$ C. to about $+5°$ C., preferably at about $0°$ C. Suitable reactive derivatives of acids of formula XV which can be used are, for example, the corresponding acid halides (e.g. acid chlorides), acid anhydrides, mixed anhydrides, activated esters, etc. When a reactive derivative is used, the reaction is conveniently carried out in an inert organic solvent such as a halogenated aliphatic hydrocarbon (e.g. dichloromethane, etc.) or an ether (e.g. diethyl ether, tetrahydrofuran, etc.) and, where appropriate, in the presence of an organic base (e.g. N-ethylmorpholine, diisopropylethylamine, etc.) at a low temperature, suitably from about $-10°$ C. to about $+5°$ C., and preferably at about $0°$ C.

The acids of formula XV above and their reactive derivatives, to the extent they are not-known compounds or analogues of known compounds, can be prepared in a similar manner to the known compounds.

EXAMPLES

The following Examples illustrate the manufacture of the alcohols of formula I.

Example 1

A stirred solution of 4.39 g (15 mmol) of 2(S)-[2-phenyl-1(S)-phthalimidoethyl]oxirane and 3.57 g (15 mmol) of N-tert.butyl-decahydro-(4aS,8aS)-isoquinoline-3(S)-carboxamide in 30 ml of dimethylformamide was heated at 120° C. for 10 hours and then left to stand at room temperature for 18 hours. The mixture was evaporated to dryness under reduced pressure. The residue was dissolved in 50 ml of ethyl acetate, washed with 30 ml of water, dried over anhydrous sodium sulphate, filtered and evaporated. The crude product was crystallized from ethyl acetate/n-hexane and there were obtained 4.77 g of N-tert.butyl-decahydro-2-[2(R)-hydroxy-4-phenyl-3(S)-phthalimidobutyl]-(4aS,8aS)-isoquinoline-3(S)-carboxamide in the form of a cream coloured solid; MS: m/e 532 [M+H]$^+$.

The 2(S)-[2-phenyl-1(S)-phthalimidoethyl]oxirane used as the starting material was prepared as follows:

(i) A mixture of 134 g of 3-phenyl-2(S)-phthalimido-propionyl chloride and 269.7 g of tris(trimethylsilyloxy)-ethylene was stirred at 95° C. for 5 hours. A further 54 g of tris(trimethylsilyloxy)ethylene were added and the mixture was stirred at 95° C. for a further 1.5 hours. The cooled reaction mixture was then treated with 435 ml of dioxan and 174 ml of 0.6N hydrochloric acid and the resulting mixture was heated to 85° C. for 30 minutes. The cooled mixture was saturated with sodium chloride and then extracted with diethyl ether. The ethereal solution was washed with aqueous sodium bicarbonate solution and evaporated. The resulting pale yellow solid was crystallized from ethyl acetate/n-hexane to give 103 g of N-[1(S)-benzyl-3-hydroxy-2-oxopropyl]phthalimide as a white solid, MS: m/e 310 [M+H]$^+$.

(ii) 100 ml of 4N hydrochloric acid in ethyl acetate were added dropwise to a stirred suspension of 120.4 g of N-[1(S)-benzyl-3-hydroxy-2-oxopropyl]phthalimide in 355 ml of dihydropyran. After 20 minutes the mixture was diluted with 500 ml of ethyl acetate, washed with sodium bicarbonate solution and sodium chloride solution and evaporated. The resulting brown oil was dissolved in 3.9 l of 10% aqueous tetrahydrofuran and the solution was stirred at–10° C. to–7° C. while 7.36 g of sodium borohydride were added. After stirring at–7° C. for 20 minutes the mixture was warmed to 0° C., a further 7.36 g of sodium borohydride were added and the stirring was continued at 0° C. for 5 minutes. The mixture was then diluted with 1 l of water and the pH was adjusted to 6 by adding concentrated hydrochloric acid. The tetrahydrofuran was removed by evaporation and the residual aqueous solution was extracted with dichloromethane. The organic solution was washed with sodium chloride solution and evaporated. The resulting brown oil was dissolved in 1.1 l of pyridine and the solution was stirred at 20° C. while 89 g of methanesulphonyl chloride were added. The mixture was stirred for a further 50 minutes and then poured on to 2 kg of crushed ice. The mixture was adjusted to pH 2 by adding concentrated sulphuric acid and was then extracted with dichloromethane. The organic solution was washed with sodium chloride solution and evaporated. The resulting brown oil was dissolved in 1 l of ethanol and treated with 11 g of p-toluenesulphonic acid. The mixture was stirred at 20° C. for 1 hour and then at 0° C. for 20 minutes. The resulting precipitate was filtered off and washed with diethyl ether to give 38.57 g of N-[1(S)-benzyl-3-hydroxy-2(R)-(methylsulphonyloxy)propyl]phthalimide as a white solid, MS: m/e 389 [M]$^+$.

(iii) 2.16 g of N-[1(S)-benzyl-3-hydroxy-2(R)-(methylsulphonyloxy)propyl]phthalimide were added to a stirred suspension of 200 mg of sodium hydride (80% dispersion in mineral oil) in 50 ml of dry tetrahydrofuran and the mixture was stirred at 20° C. for 2 hours. A further 100 mg of sodium hydride were added and the stirring was continued for 3.5 hours. The mixture was diluted with dichloromethane and water and the pH of the aqueous layer was adjusted to 7 by adding 2M hydrochloric acid. The organic layer was separated, washed with saturated sodium chloride solution and evaporated. The residue was chromatographed on silica gel using ethyl acetate/n-hexane (1:2) for the elution to give 0.67 g of 2(S)-[2-phenyl-1(S)-phthalimidoethyl]oxirane as a white solid, MS: m/e 294 [M+H]$^+$.

The N-tert.butyl-decahydro-(4aS,8aS)-isoquinoline-3(S)-carboxamide used as the starting material was prepared as follows:

(i) A suspension of 12.676 g (71.6 mmol) of 1,2,3,4-tetrahydro-3(S)-isoquinolinecarboxylic acid (Chem. Pharm. Bull. 1983, 31, 312) in 200 ml of 90% acetic acid was hydrogenated at 80° C. and under 140 atmospheres pressure over 5% rhodium-on-carbon for 24 hours. The mixture was left to cool to room temperature and the catalyst was then filtered off. The filtrate was evaporated to give a gum which was dissolved in 10 ml of ethyl acetate and added slowly to 100 ml of vigorously stirred diisopropyl ether. A resinous precipitate was produced. The supernatant liquors were removed by decantation and the precipitate was extracted with hot ethyl acetate. This hot solution was poured into a vigorously stirred mixture of 150 ml of diethyl ether/diisopropyl ether (1:1) to give a pale grey solid which was collected by filtration, washed with diethyl ether and dried. There were obtained 5.209 g of a mixture of decahydroisoquinoline-3(S)-carboxylic acids consisting of predominantly (about 65%) the 4aS, 8aS isomer together with the 4aR,8aR isomer (about 25%) and about 10% of the trans isomers; MS: m/e 184 [M+H]$^+$.

(ii) 9.036 g (49.4 mmol) of the foregoing mixture of decahydroisoquinoline-3(S)-carboxylic acids were dissolved in 50 ml (50 mmol) of 1M sodium hydroxide solution and the resulting solution was cooled to 0° C. 7.40 ml (51.87 mmol) of benzyl chloroformate and 58.7 ml (58.7 mmol) of 1M sodium hydroxide solution were added dropwise over a period of 1 hour while maintaining a temperature of 0–5° C. by cooling. The mixture was then stirred for a further 2 hours, during which time the mixture was allowed to warm to room temperature. 100 ml of diethyl ether were added and the mixture was filtered, whereby the insoluble R,R-isomer was removed. The aqueous layer of the filtrate was separated and adjusted to pH 1.5–2 by the addition of concentrated hydrochloric acid, whereby an oil precipitated. The mixture was extracted twice with 100 ml of ethyl acetate each time. The combined organic extracts were washed with water, dried over anhydrous sodium sulphate and evaporated to give an oil. This oil was dissolved in 35 ml of ethyl acetate and 2.85 ml (25 mmol) of cyclohexylamine were added. The white precipitate was collected by filtration to give, after several fractional recrystallizations from methanol/ethyl acetate, 2.38 g of the cyclohexylamine salt of 2-(benzyloxycarbonyl)-decahydro-(4aS,8aS)-isoquinoline-3(S)-carboxylic acid; MS: m/e 318 [M+H]$^+$.

(iii) 2.384 g of the cyclohexylamine salt of 2-(benzyloxycarbonyl)-decahydro-(4aS,8aS)-isoquinoline-3(S)-carboxylic acid were partitioned between 50 ml of ethyl acetate and 50 ml of 10% citric acid solution. The organic phase was separated, washed with water, filtered and evaporated to give 1.87 g of 2-(benzyloxycarbonyl)-decahydro-(4aS,8aS)-isoquinoline-3(S)-carboxylic acid in the form of a colourless gum; MS: m/e 318 [M+H]$^+$.

(iv) A solution of 0,634 g (2.0 mmol) of 2-(benzyloxycarbonyl)-decahydro-(4aS,8aS)-isoquinoline-3(S)-carboxylic acid in 6 ml of dimethoxyethane was treated with 0.23 g (2.0 mmol) of N-hydroxysuccinimide and 0.412 g (2.0 mmol) of dicyclohexylcarbodiimide. The mixture was stirred at room temperature for 18 hours. The mixture was filtered and the filtrate was evaporated to give 0.879 g of the N-hydroxysuccinimide ester of the foregoing acid in the form of a pale yellow oil. A solution of 0.828 g (2.0 mmol) of the foregoing N-hydroxysuccinimde ester in 5 ml of dichloromethane was stirred, cooled to 0° C. and treated with 0.219 g (3.0 mmol) of tert.butylamine. The mixture was stirred at 0° C. for 2 hours and then at room temperature for 4.5 hours. The mixture was then washed with 2M hydrochloric acid, sodium carbonate solution and sodium chloride solution, dried over anhydrous magnesium sulphate and evaporated. The residue was dissolved in 20 ml of diethyl ether and filtered. The filtrate was evaporated to give 0.712 g of 2-(benzyloxycarbonyl)-N-tert.butyl-decahydro-(4aS,8aS)-isoquinoline-3(S)-carboxamide in the form of a pale yellow glass; MS: m/e 373 [M+H]$^+$.

(V) A solution of 0.689 g (1.85 mmol) of 2-(benzyloxycarbonyl)-N-tert.butyl-decahydro-(4aS,8aS)-isoquinoline-3(S)-carboxamide in 20 ml of ethanol was hydrogenated in the presence of 0.01 g of 10% palladium-on-carbon at room temperature and under atmospheric pressure for 18 hours. The catalyst was removed by filtration and the solvent was removed by evaporation to give 1.85 mmol of N-tert.butyl-decahydro-(4aS,8aS)-isoquinoline-3(S)-carboxamide as a clear oil: MS: m/e 239 [M+H]$^{30}$, which was used in the next step without further purification.

Example 2

A mixture of 0.378 g (2 mmol) of 2(S)-[1(S)-azido-2-phenylethyl]oxirane and 0.476 g (2 mmol) of N-tert.butyl-decahydro-(4aS,8aS)-isoquinoline-3(S)-carboxamide in 10 ml of ethanol was stirred and boiled under reflux for 5 hours and then left to stand at room temperature for 18 hours. The mixture was evaporated to dryness under reduced pressure and the pale yellow solid obtained was crystallized from ethyl acetate/n-hexane (1:1) to give 0.593 g of a white solid. Recrystallization from the same solvent mixture gave 0.165 g of 2-[3(S)-azido-2(R)-hydroxy-4-phenylbutyl]-N-tert.butyl-decahydro-(4aS,8aS)-isoquinoline-3(S)-carboxamide: MS: m/e 428 [M+H]$^+$.

The 2(S)-[1(S)-azido-2-phenylethyl]oxirane used as the starting material was prepared as follows:

(i) 4.34 g (0.02 mol) of (2R,3R)-2-benzyloxybutane-1,3,4-triol were suspended in a mixture of 3.4 g (0.02 mmol) of 1-cyclohexenyloxytrimethylsilane and 40 ml of diethyl ether. Two drops of concentrated hydrochloric acid were added and the mixture was stirred at room temperature for 30 minutes. The mixture was then evaporated to give 5.65 g of β(R)-benzyloxy-1,4-dioxaspiro[4,5]decane-2(R)-ethanol in the form of a colourless viscous oil; MS: m/e 292 [M]$^+$.

(ii) 15.0 g of pyridinium chlorochromate and 10.0 g of crushed 3A molecular sieves were added to a solution of 5.50 g (0.019 mol) of β(R)-benzyloxy-1,4-dioxaspiro[4,5]-decane-2(R)-ethanol in 200 ml of dichloromethane. The mixture was stirred at room temperature for 20 hours, then diluted with 200 ml of diethyl ether and filtered. The filtrate was evaporated to give 4.30 g of α(S)-benzyloxy-1,4-dioxaspiro[4,5]decane-2(R)-acetaldehyde which was used in the next step without further purification.

(iii) A solution of 4.30 g (0.015 mmol) of α(S)-benzyloxy-1,4-dioxaspiro[4,5]decane-2(R)-acetaldehyde in 50 ml of anhydrous diethyl ether was cooled to −8° C. and 15 ml of a 2M solution of phenylmagnesium chloride in tetrahydrofuran were added dropwise over a period of 1 hour. The mixture was stirred at−5° C. for 2 hours then allowed to warm to room temperature and poured into 50 ml of 10% ammonium chloride solution. The mixture was extracted twice with 100 ml of ethyl acetate each time. The ethyl acetate extracts were dried over anhydrous magnesium sulphate and evaporated. The residue was subjected to flash chromatography on silica gel using 5% methanol in dichloromethane for the elution. There were obtained 2.47 g of β(R)-benzyloxy-α(RS)-phenyl-1,4-dioxaspiro[4,5]decane-2(R)-ethanol in the form of a colourless gum; MS (C.I.): m/e 369 [M+H]$^+$.

(iv)(a) A solution of 130 mg (0.35 mmol) of β(R)-benzyloxy-α(RS)-phenyl-1,4-dioxaspiro[4,5]decane-2(R)-ethanol in 3 ml of acetic acid was hydrogenated over 10% palladium-on-carbon under a pressure of about 4.1 atmospheres for 2 days. The catalyst was removed by filtration and the filtrate was evaporated. The crude product was purified by flash chromatography on silica gel using 2% methanol in dichloromethane for the elution. There were obtained 60 mg of α(R)-benzyl-1,4-dioxaspiro-[4,5]decane-2(R)-methanol in the form of a colourless oil; MS: m/e 262 [M]$^+$.

(iv)(b) A solution of 80 mg (0.22 mmol) of β(R)-benzyloxy-α(RS)-phenyl-1,4-dioxaspiro-[4,5]decane-2(R)-ethanol and 50 mg (0.49 mmol) of acetic anhydride in 1 ml of pyridine was stirred at room temperature for 20 hours. Solvents were removed by evaporation to give 80 mg of β(R)-benzyloxy-α(RS)-phenyl-1,4-dioxaspiro[4,5]decane-2(R)-ethyl acetate in the form of a colourless oil; MS: m/e 410 [M]$^+$.

A solution of 80 mg of β(R)-benzyloxy-α(RS)-phenyl-1,4-dioxaspiro[4,5]decane-2(R)-ethyl acetate in 3 ml of acetic acid was hydrogenated over 10% palladium-on-carbon under a pressure of about 4.8 atmospheres of hydrogen for 2 days. The catalyst was removed by filtration and the filtrate was evaporated. The crude product was subjected to flash chromatography on silica gel using 2% methanol in dichloromethane for the elution. There were obtained 33 mg of α(R)-benzyl-1,4-dioxaspiro[4,5]decane-2(R)-methanol in the form of a colourless oil; m/e.262 [M]$^+$.

(v) A mixture of 65 mg (0.25 mmol) of α(R)-benzyl-1,4-dioxaspiro]4,5]decane-2(R)-methanol, 65 mg (0.28 mmol) of triphenylphosphine and 80 mg (1.2 mmol) of sodium azide in 1 ml of dimethylformamide was cooled to 0° C. and 83 mg (0.25 mmol) of carbon tetrabromide were added. The mixture was stirred at room temperature overnight. 0.5 ml of methanol was added and the mixture was stirred for 15 minutes and then evaporated to dryness. The residue was partitioned between 10 ml of ethyl acetate and 10 ml of water, the organic phase was separated, dried over anhydrous magnesium sulphate and evaporated. The residue was purified by flash chromatography on silica gel using 20% ethyl acetate in n-hexane for the elution. There were obtained 48 mg of 2(S)-[1(S)-azido-2-phenylethyl]-1,4-dioxaspiro[4,5]decane as a colourless oil; MS (C.I.): m/e 260 [M+H-N2]$^+$ (vi) A solution of 138 mg (0.48 mmol) of 2(S)-[1(S)-azido-2-phenylethyl]-1,4-dioxaspiro[4,5]decane in a mixture of 8 ml of acetic acid and 2 ml of water was stirred at 100° C. for 2 hours. The solvent was removed by evaporation and the residue was partitioned between 15 ml of ethyl acetate and 10 ml of saturated sodium bicarbonate solution. The organic phase was dried over anhydrous magnesium sulphate and evaporated to give 85 mg of a white solid. This was suspended in 5 ml of 10% ethyl acetate in n-hexane, stirred for 15 minutes and filtered to give 34 mg of 3(S)-azido-4-phenyl-1,2(S)-butanediol in the form of a white solid of melting point 83°–84° C.

(vii) 1.05 g (5.5 mmol) of p-toluenesulphonyl chloride were added to a solution of 0.95 g (4.6 mmol) of 3(S)-azido-4-phenyl-1,2(S)-butanediol and 30 mg of 4-dimethylaminopyridine in a mixture of 30 ml of dichloromethane and 5 ml of pyridine. The resulting solution was stirred at room temperature for 48 hours. The solvents were removed under reduced pressure and the oily residue was partitioned between water and ethyl acetate. The aqueous phase was back-extracted twice with ethyl acetate. The organic phases were combined, washed with 10% aqueous sulphuric acid and with sodium chloride solution, dried over anhydrous magnesium sulphate and evaporated to dryness. Purification of the crude product by flash chromatography on silica gel using n-hexane/ethyl acetate (3:1) for the elution gave 1.37 g of 3(S)-azido-4-phenyl-1-(p-toluenesulphonyloxy)-2(S)-butanol in the form of a viscous oil MS: m/e 362 [M+H]$^+$.

(viii) A solution of 280 mg (5 mmol) of potassium hydroxide in 10 ml of ethanol were added to a solution of 1.37 g (3.8 mmol) of 3(S)-azido-4-phenyl-1-(p-toluenesulphonyloxy)-2(S)-butanol in 50 ml of ethanol and the mixture was stirred at room temperature for 1 hour. The mixture was then evaporated to dryness and the residue was partitioned between water and dichloromethane. The aqueous phase was back-extracted twice with dichloromethane. The organic phases were combined, dried over anhydrous magnesium sulphate and evaporated to give an oil which was purified by flash chromatography on silica gel using n-hexane/ethyl acetate (4:1) for the elution. There was obtained 0.47 g of 2(S)-[1(S)-azido-2-phenylethyl]oxirane: MS: m/e 189 [M]$^-$.

Example 3

A solution of 237 mg (1 mmol) of N-tert.butyl-decahydro-(4aS,8aS)-isoquinoline-3(S)-carboxamide and 300 mg (1.1 mmol) of 4(S)-[1(S)-azido-2-phenylethyl]-1,3,2-dioxathiolane 2,2-dioxide in 10 ml of tetrahydrofuran was stirred at room temperature under an argon atmosphere for 2 days, during which time some white solid deposits formed. The mixture was evaporated to give a white powder which was taken up in a 10% solution of sulphuric acid in 70% aqueous methanol and heated under reflux for 30 minutes. After cooling to room temperature the solution was adjusted to pH 10 with 10% aqueous sodium hydroxide solution and extracted three times with ethyl acetate. The ethyl acetate extracts were combined, washed with sodium chloride solution, dried over anhydrous magnesium sulphate and evaporated. Purification of the crude product by flash chromatography on silica gel using n-hexane/ethyl acetate (4:1) for the elution gave 57 mg of 2-[3(S)-azido-2(R)-hydroxy-4-phenylbutyl]-N-tert.butyl-decahydro-(4aS,8aS)-isoquinoline-3(S)-carboxamide; MS: m/e 428 [M+H]$^+$.

The 4(S)-[1(S)-azido-2-phenylethyl]-1,3,2,-dioxothiolane 2,2-dioxide used as the starting material was prepared as follows:

175 µl (2.4 mmol) of thionyl chloride were added to a solution of 414 mg (2 mmol) of 3(S)-azido-4-phenyl-1,2(S)-butanediol [prepared as described in Example 2(vi)] in 5 ml of carbon tetrachloride and the mixture was heated under reflux for 30 minutes with calcium chloride drying tube protection. The resulting solution was cooled in an ice bath, 5 ml of acetonitrile, 5 mg of ruthenium-(III) chloride trihydrate, 642 mg (3 mmol) of sodium metaperiodate and 7.5 ml of water were added in succession and the mixture was stirred vigorously at room temperature for 1 hour. The mixture was treated with 20 ml of diethyl ether and 20 ml of water, the phases were separated and the aqueous phase was extracted twice with diethyl ether. The organic phases were combined and washed with water, saturated aqueous sodium bicarbonate solution and sodium chloride solution. After drying over anhydrous magnesium sulphate, filtration through diatomaceous earth and evaporation of the filtrate there were obtained 518 mg of 4(S)-[1(S)-azido-2-phenylethyl]-1,3,2-dioxathiolane 2,2-dioxide; MS: m/e 270 [M+H]$^+$.

The following Example illustrates the manner in which the alcohols of formula I can be converted into amino acid derivatives of formula II:

Example 4

(A)(i) A mixture of 25.6 g (48.3 mmol) of N-tert.butyl-decahydro-2-[2(R)-hydroxy-4-phenyl-3(S)-phthalimidobutyl]-(4aS,8aS)-isoquinoline-3(S)-carboxamide (prepared as described in Example 1) and 3.74 ml (96.5 mmol) of hydrazine hydrate in 145 ml of ethanol was stirred at room temperature for 4 hours. The mixture was evaporated to dryness under reduced pressure. The residue was dissolved in toluene and the solution was evaporated, this procedure being repeated once. The residue was then dissolved in 2M acetic acid and the solution was stirred at room temperature for 1 hour. The mixture was filtered and the filtrate was basified by the addition of solid sodium carbonate and then extracted twice with dichloromethane. The combined dichloromethane extracts were washed with sodium chloride solution, filtered and evaporated to give a brown solid which was triturated with diethyl ether. There were thus obtained 12.93 g of 2-[3(S)-amino-2(R)-hydroxy-4-phenylbutyl]-N-tert.butyl-decahydro-(4aS,8aS)-isoquinoline-3(S)-carboxamide as a white solid; MS: m/e 402 [M+H]$^+$.

(A)(ii) A suspension of 26.55 g of N-tert.butyl-2-[2(R)-hydroxy-4-phenyl-3(S)-phthalimidobutyl]-(4aS,8aS)-isoquinoline-3(S)-carboxamide (prepared as described in Example 1) in 100 ml of ethanol was treated with 25 ml of a 30% solution of methylamine in ethanol at room temperature for 1 hour. The mixture was evaporated to dryness under reduced pressure. The residue was dissolved in 250 ml of ethanol, treated with 250 ml of a saturated solution of hydrogen chloride in ethyl acetate and stirred at room temperature for 16 hours. The mixture was evaporated to dryness and the residue was partitioned between ethyl acetate and water. The aqueous phase was separated, made basic with solid sodium carbonate and then extracted with dichloromethane. The dichloromethane extract was washed with sodium chloride solution and evaporated to dryness. The residue was triturated with diethyl ether and, after filtration, there were obtained 17.48 g of 2-[3(S)-amino-2(R)-hydroxy-4-phenylbutyl]-N-tert.butyl-decahydro-(4aS,8aS)-isoquinoline-3(S)-carboxamide as a white solid; MS: m/e 402 [M+H]$^+$.

(A)(iii) A solution of 17 mg (0.04 mmol) of 2-[3(S)-azido-2(R)-hydroxy-4-phenylbutyl]-N-tert.butyl-decahydro--(4aS,8aS)-isoquinoline-3(S)-carboxamide (prepared as described in Example 2 or Example 3) in 5 ml of ethanol was hydrogenated at about 3.4 atmospheres and at room temperature for 2 hours over 10 mg of 10% palladium-on-charcoal. The catalyst was filtered off and washed twice with ethanol. The combined filtrate and washings were evaporated to give 16 mg of 2-[3(S)-amino-2(R)-hydroxy-4-phenylbutyl]-N-tert.butyl-decahydro-(4aS,8aS)-iso quinoline-3(S)-carboxamide; MS: m/e 402 [M+H]$^+$.

(B) A solution of 561 mg of 2-[3(S)-amino-2(R)-hydroxy-4-phenylbutyl]-N-tert.butyl-decahydro-(4aS,8aS)-isoquinoline-3(S)-carboxamide and 372 mg of N-(benzyloxycarbonyl)-L-asparagine in 20 ml of dry tetrahydrofuran was cooled in an ice/salt mixture. 189 mg of hydroxybenzotriazole, 161 mg of N-ethylmorpholine and 317 mg of dicyclohexylcarbodiimide were added and the mixture was stirred for 16 hours. The mixture was then diluted with ethyl acetate and filtered. The filtrate was washed with aqueous sodium bicarbonate solution and sodium chloride solution. The solvent was removed by evaporation and the residue was chromatographed on silica gel using dichloromethane/ methanol (9:1) for the elution to give 434 mg of 2-[3(S)-[ [N-(benzyloxycarbonyl)-L-asparaginyl]amno]-2(R)-hydroxy-4-phenylbutyl ]-N-tert.butyl-decahydro (4aS,8aS)-isoquinoline-3(S)-carboxamide as a white solid from methanol/diethyl ether; MS: m/e 650 [M+H]$^+$.

Example 5

A solution of 287 mg of N-(2-quinolylcarbonyl)-L-asparagine and 401 mg of 2-[3(S)-amino-2(R)-hydroxy-4 -phenylbutyl]-N-tert.butyl-decahydro-(4aS,8aS)-isoquinoline-3(S)-carboxamide in 3 ml of tetrahydrofuran was cooled to −10° C. and 163 mg of 3-hydroxy-1,2,3-benzotriazin-4(3H)-one and 220 mg of dicyclohexylcarbodiimide were added. The mixture was stirred at−10° C. for 2 hours and at 20° C. for 16 hours, then diluted with ethyl acetate and filtered. The filtrate was washed with saturated sodium bicarbonate solution and saturated sodium chloride solution and then evaporated. The residue was chromatographed on silica gel using 4% (by volume) methanol in dichloromethane for the elution to give 537 mg of N-tert.butyl-decahydro-2-[2(R)-hydroxy-4-phenyl-3(S)-[[N-(2-quinolylcarbonyl)-L-asparaginyl]amino]butyl]-(4aS,8aS)-isoquinoline-3(S)-carboxamide as a white solid: MS: m/e 671 [M+H]$^+$.

The N-(2-quinolylcarbonyl)-L-asparagine used as the starting material was prepared as follows:

A mixture of 540 mg of quinaldic acid succinimide ester and 300 mg of L-asparagine monohydrate in 2 ml of dimethylformamide was stirred at 20° C. for 96 hours. The solvent was removed by evaporation to give a white solid residue which was stirred vigorously in 10 ml of dichloromethane, filtered off and washed with dichloromethane. There were thus obtained 431 mg of N-(2-quinolylcarbonyl)-L-asparagine as a white solid; MS: m/e 288[M+H]$^+$.

We claim:

1. A compound of formula

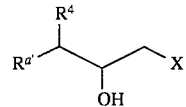

VII wherein $R^{a'}$ is azido, $R^4$ is alkyl, cycloalkyl, cycloalkylalkyl, aryl or aralkyl and X is a leaving atom or group.

2. A compound of claim 1 wherein X is a halogen atom, an alkanesulphonyloxy group, or an aromatic sulphonyloxy group.

* * * * *